(12) United States Patent
Masuyama et al.

(10) Patent No.: US 6,596,301 B1
(45) Date of Patent: Jul. 22, 2003

(54) ANTI-STRESS DRUGS AND FUNCTIONAL FOODS HAVING ANTI-STRESS EFFECTS

(75) Inventors: Akihiro Masuyama, Yokohama (JP); Masaaki Yasui, Yokohama (JP)

(73) Assignees: Danone, Groupe, Paris (FR); Calpis Co., Ltd., Tokyo (JP)

(*) Notice: Subject to any disclaimer, the term of this patent is extended or adjusted under 35 U.S.C. 154(b) by 0 days.

(21) Appl. No.: 09/242,239

(22) PCT Filed: Aug. 6, 1997

(86) PCT No.: PCT/JP97/02728

§ 371 (c)(1),
(2), (4) Date: Feb. 5, 1999

(87) PCT Pub. No.: WO98/05343

PCT Pub. Date: Feb. 12, 1998

(30) Foreign Application Priority Data

Aug. 7, 1996 (JP) .............................................. 8-208504

(51) Int. Cl.[7] ......................... A61K 47/00; A61K 38/00; A23C 9/12; A23C 9/16
(52) U.S. Cl. ............................. 424/439; 514/2; 426/62; 426/588
(58) Field of Search ...................... 14/2; 426/61, 62, 426/580–588; 424/439

(56) References Cited

U.S. PATENT DOCUMENTS

| 5,449,661 A | * | 9/1995 | Nakamura et al. | ............ 514/15 |
| 5,972,393 A | | 10/1999 | Beutler et al. | ................ 426/34 |

FOREIGN PATENT DOCUMENTS

| JP | 61-153216 | 3/1986 |
| JP | 4-5236 | 1/1992 |
| JP | 7-123977 | 5/1995 |

OTHER PUBLICATIONS

Nakamura et al. "Decrease of Tissue Angiotensin I–Converting Enzyme Activity upon Feeding sour milk in Sponteneously hypertensive rats," 1996, Biosci. Biotech. Biochem. vol. 60, No. 3, pp. 488–489.*
Merck Manual, Fifteenth Edition, Merck Sharp & Dohme, 1987, pp. 1462–1467, 1512–1533.*
CAPLUS Abstract, AN 1996:198357, Nakamura et al. 1996.*
MEDLINE Abstract, AN 84127335, Materia et al. 1984.*
FSTA Abstract, AN 1981 (06):p0950, 1981, Baltadzieva et al.*
Medline Abstract, AN 85120823, 1985, Prattala et al.*
ATCC8205 Data, American Type Culture Collection, Jan., 2000.*
Kabayama et al. "Effects of food components on the immunoresponse of animal cells suppressed by stress hormes," Proc. Annu. Meet. Jpn. Assoc. Anim. Cell Technol (1995), 1997 (Abstract) CAPLUS AN:1997:563337.*
Osada et al. "Enhancement of interferon–beta production with sphinogomyelin from fermented milk," Biotherapy 1993–94; 7 (2), pp. 115–123 (Abstract) Pubmed Medline Abstract.*

* cited by examiner

Primary Examiner—Russell Travers
Assistant Examiner—Shengjun Wang
(74) Attorney, Agent, or Firm—Darby & Darby

(57) ABSTRACT

An anti-stress agent and functional food containing the anti-stress agent and having an anti-stress effect, which contain as an effective ingredient fermented sour milk prepared by, for example, fermenting animal milk starting material with lactic acid bacteria of the genus Lactobacillus, which can be taken repeatedly and daily without any problems with safety, and which can mitigate and prevent mental and physical symptoms caused by stress.

3 Claims, 2 Drawing Sheets

ANTI-STRESS DRUGS AND FUNCTIONAL FOODS HAVING ANTI-STRESS EFFECTS

This application is a 371 of PCT/JP97/02728, filed Aug. 6, 1997, which claims the priority of JP application 8-208504, filed Aug. 7, 1996.

FIELD OF ART

This invention relates to an anti-stress agent having effects of preventing and mitigating mental and physical symptoms caused by stress, and functional food containing the anti-stress agent which is prepared by adding the anti-stress agent to yogurt, milk-containing acidified beverages, cheese, various processed foods, healthy foods, powdered foods, or granulated foods to give an anti-stress effect thereto.

BACKGROUND ART

In the modern society, people undergo various kinds of stress caused by highly advanced and complicated scientific technology, or drastically changing social circumstances. Particularly, in the internationalized society, complex human relationships are formed, causing mental stress. It has been reported that a variety of symptoms are caused by mental stress.

It is recognized that mental stress has a great influence on circulatory system. However, the scientific concept and definition of stress have not yet been well established, so that means of evaluation of stress still have many problems, combined with methodological difficulties. However, in the recent years, studies of stress have been made from the medical point of view.

For example, it is reported that when one undergoes stress, angiotensins II and/or vasopressin increase, and intracorporeal sodium due to sodium reabsorbancy becomes excess, which causes rise in blood pressure (Osamu Mobara et al.: Taisha, 28, 2, 323, 1991). However, suffering stress not only causes rise in blood pressure, but also influences various factors, such that it is believed to cause stomach ulcer, ischemic cardiac diseases, cerebrovascular diseases, hypertension, hyperlipemia, or the like. Therefore, though the investigation of the relationship between stress and hypertension is of importance, it is not believed that mere lowering of blood pressure will bring about the anti-stress effect.

As an agent for preventing and mitigating mental and physical symptoms caused by stress, chemically synthesized medicaments such as a tranquilizer, an antianxiety agent, and sleeping pills are presently used. However, these medicaments have habituation and side effect problems, so that it is not preferable to use them daily for the purpose of preventing mental and physical symptoms caused by stress. Accordingly, foods having the anti-stress effect are desired and are under development, which can be taken repeatedly and daily without any problems with safety, and which can mitigate and prevent mental and physical symptoms caused by stress. For example, an anti-stress agent containing as an effective ingredient L-theanine contained in tea leaves, is proposed in Japanese Laid-open Patent Application No. 6-100442, which can be mixed in tasty beverages (nutrient supplementary drinks) for daily uptake. Further, a stress relieving effect of fragrance is also reported (FRAGRANCE JOURNAL:1991-11, 44). However, there has not been reported that lactic acid bacteria-fermented milk has the effect of mitigating and preventing mental and physical symptoms caused by stress.

DISCLOSURE OF THE INVENTION

It is therefore an object of the present invention to provide an anti-stress agent which can fulfill the social demand as mentioned above, which can be taken repeatedly and daily without any problems with safety, and which can mitigate and prevent mental and physical symptoms caused by stress; and its use.

It is another object of the present invention to provide functional food having an anti-stress effect which can fulfill the social demand as mentioned above, and which can be taken as food repeatedly and daily without any problems with safety; and its use.

The present inventors have made intensive studies to find a substance which can fulfill the social demand as mentioned above, which can be used in food, and which can be taken repeatedly without any problems with safety. As a result, they have noticed that fermented sour milk has a superior anti-stress effect, and completed the present invention.

According to the present invention, there is provided an anti-stress agent containing as effective agent at least one fermented sour milk.

According to the present invention, there is also provided a functional food having anti-stress effect containing the anti-stress agent.

According to the present invention, there is further provided use of the anti-stress agent or the functional food for the manufacture of a drug for the treatment of stress.

According to the present invention, there is also provided a method of treatment of human or animal stress comprising oral administration of the anti-stress agent or the functional food.

PREFERRED EMBODIMENTS OF THE INVENTION

Figure 1:
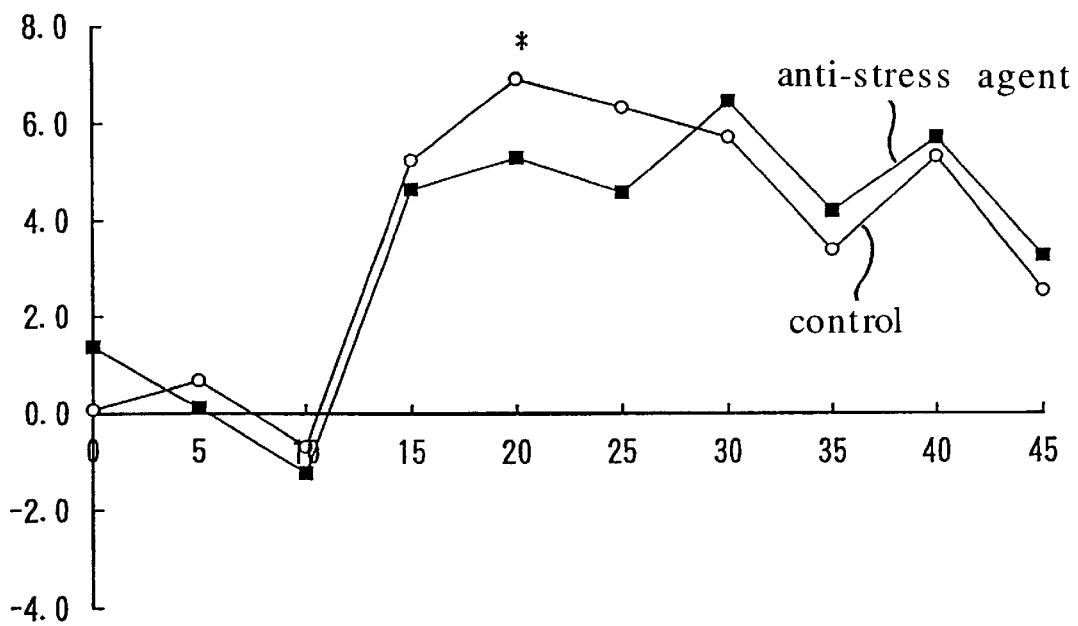
FIG. 1 is a graph showing the fluctuation in the diastolic blood pressure during the testing period of the mental arithmetic test in Experiment 1 in Example 1. The ordinate of the graph expresses the diastolic blood pressure in mmHg, while the abscissa expresses the time in minute.

The anti-stress agent of the present invention contains at least one fermented sour milk as effective agent having an anti-stress effect. The anti-stress effect of this anti-stress agent can be confirmed, employing the rise in blood pressure, the rise in heart rate, and the change in Profile of Mood State (POMS), or the like as the indices, by determining the suppressing effects of the agent upon such rises and changes taken before and after the intake of the agent.

As the fermented sour milk contained as effective agent in the anti-stress agent of the present invention, lactic acid bacteria-fermented milk is used, of which great safety in its repeated daily use has conventionally been confirmed. The fermented sour milk maybe prepared, for example, by first preparing a milk-containing stock solution.

The milk contained in the milk-containing stock solution may be of animal or vegetable origin. For example, animal milk such as cow's milk, goat's milk, sheep's milk, or horse's milk; or vegetable milk from soybeans or the like, may be used. The milk starting material may be whole fat or skim milk, whey, powdered milk, and/or reconstituted milk.

The milk-containing stock solution is not limited to a liquid wherein milk is dissolved or suspended and dispersed. The stock solution may be a solution-containing material such as paste prepared by mixing milk powders or a milk-containing material with water or a solution of salts. Additionally, a medium for lactic acid bacteria, yeast extracts, vitamins, minerals, sugars, lipids, flavors, or coloring agents may optionally be contained in the milk-containing stock solution.

Subsequently, the milk-containing stock solution is fermented with lactic acid bacteria, or symbiotically fermented with lactic acid bacteria and yeast for the purpose of improving flavor of the produced functional food, thereby obtaining the fermented sour milk.

The lactic acid bacteria are preferably lactic acid bacteria of the genus Lactobacillus. For example, *Lactobacillus helveticus, Lactobacillus delbruekii*subsp. *bulgaricus, Lactobacillus acidophilus, Lactobacillus fermentum*, or *Lactobacillus casei* subsp. *casei* may be used. Specifically, a strain such as *Lactobacillus helveticus* ATCC55796, *Lactobacillus delbruekii* subsp. *bulgaricus* ATCC11842, *Lactobacillus acidophilus* ATCC4356, *Lactobacillus fermentum* ATCC14931, or *Lactobacillus casei* subsp. *casei* ATCC393 may be used. Among these, *Lactobacillus helveticus* is particularly preferred.

The yeast which can be used for symbiotic fermentation with the lactic acid bacteria may be yeast of the genus Saccharomyces, genus Candida, or the genus Kluyveromyces. For example, a strain such as *Saccharomyces cerevisiae, Candida utilis*, or *Kluyveromyces marxianus* var. *lactis* may be used.

Culture conditions for fermentation include sterilizing the milk-containing stock solution under heating, cooling the sterilized stock solution to the predetermined culturing temperature, and admixing a starter consisting of previously cultured lactic acid bacteria, or of previously cultured lactic acid bacteria and the yeast, to the stock solution. The culturing temperature may be 20 to 50° C., preferably 30 to 45° C., and the culturing time may be 3 to 48 hours, preferably 6 to 24 hours. Termination of the culture can be determined with the number of lactic acid bacteria of $10^8$ cells/g or more, and the acidity of the lactic acid of 1 or higher. The amount of the lactic acid bacteria starter to be inoculated for the culture is preferably $10^5$ cells/g to $10^7$ cells/g in terms of lactic acid bacteria with respect to the medium.

The anti-stress agent of the present invention may be in the form of the above cultured solution per se containing the fermented sour milk as an effective ingredient, or in the form of the cultured solution from which components other than fermented sour milk and lactic acid bacteria have suitably been separated. In either case, the lactic acid bacteria or the lactic acid bacteria together with the yeast therein are kept alive, i.e., in a live form. Alternatively, the cultured solution or the separated cultured solution may be sterilized under heating up to 80° C. to prepare an anti-stress agent in a sterilized form. Further, the above sterilized or non-sterilized cultured solution may be purified to obtain fermented sour milk; may be powdered by lyophilizing, spray drying, or drying in a drum dryer; or may further be formed into tablets using vehicles or carriers.

The anti-stress agent of the present invention may be administered orally to human or animals at any time such as before suffering stress, under stress, and after suffering stress, and may be administered even daily. The upper limit of the effective dose of the anti-stress agent is not particularly limited, and may suitably be selected. But the effective dose for sufficiently mitigating and preventing stress is, when the anti-stress agent is administered to human, preferably not less than 0.1 g per kilogram of body weight per day in terms of dried product of the fermented sour milk.

The functional food having the anti-stress effect of the present invention contains the above-mentioned anti-stress agent. Therefore, the anti-stress agent contained therein may be in the form of the cultured solution per se as mentioned above or after the suitable processing, with the lactic acid bacteria or the lactic acid bacteria together with the yeast being alive; in the sterilized form prepared by sterilizing under heating up to 80° C.; or in the powdered form prepared by lyophilizing, spray drying, or drying in a drum dryer.

The functional food of the present invention is not particularly limited as long as it contains the anti-stress agent as mentioned above. The anti-stress agent may be added after the food production, during the food production, or at any stage of the food production. Further, the functional food of the present invention may suitably contain sugars, proteins, lipids, vitamins, minerals, flavors, or coloring agents in addition to the anti-stress agent, depending on the type of the food.

The amount of the anti-stress agent contained in the functional food of the present invention is not particularly limited, but is usually in the preferred range of 10 to 100 w/w % in terms of fermented sour milk.

The functional food of the present invention may be in the form of yogurt, milk-containing acidified beverages, cheese, processed foods containing fermented sour milk, healthy foods, or powdered or granulated foods.

The effective amount of the functional food of the present invention for mitigating and preventing stress is, in the case of human, preferably not less than 0.1 g per kilogram of body weight per day in terms of dried product of the fermented sour milk.

The anti-stress agent and the functional food of the present invention can be used for manufacture of a drug for the treatment of stress in the form of solid or liquid, specifically, in the form of tablets, granules, or nutrient supplementary drinks.

The anti-stress agent and the functional food having the anti-stress effect of the present invention contain as effective agent fermented sour milk prepared by fermentation with lactic acid bacteria. Accordingly, they are highly safe, can be ingested repeatedly and daily, and have effects of mitigating and preventing mental and physical symptoms caused by stress.

EXAMPLES

The present invention will now be explained in more detail with reference to Examples, but the present invention is not limited thereto.

Example 1

2 kg of skim milk (solid content of 9 weight %) sterilized by heating up to 90° C. were inoculated with 40 g of a starter of previously cultured *Lactobacillus helveticus* ATCC55796, and cultured at 37° C. for 24 hours to prepare the secondary starter. Next, 4.5 kg of skim milk powders were dissolved in 45.5 kg of water, and the resulting solution was sterilized by heating up to 90° C. and cooled down to the room temperature. Then the solution was inoculated with the secondary starter, and cultured at 37° C. for 24 hours to obtain about 52 kg of fermented sour milk. After sterilizing the fermented sour milk at 80° C. for 10 minutes by heating, Aspartame (trade name, manufactured by Ajinomoto K.K.) was admixed to the fermented sour milk in an amount of 0.04 weight % of the total weight for facilitating drinking, thereby obtaining an anti-stress agent. As to the obtained anti-stress agent, the following experiments were conducted.

Experiment 1

The above mentioned anti-stress agent and a control consisting of a mixture of skim milk and lactic acid of the same concentration as the fermented sour milk, were given as a drink to fifteen (15) panels of healthy individuals (7 males, 8 females, age of 24 to 32), and mental arithmetic test as described below was conducted on the panels.

The panels were given one of the anti-stress agent and the control in an amount of 100 g each at 6:00 p.m. and 12:00 p.m. on the day before the measurement, 7:00 a.m. on the day of the measurement, and 30 minutes before the commencement of the test (10:00 a.m.), i.e. a total of four (4) times in a total amount of 400 g. Then on a different set of days, the panels were given the other of the anti-stress agent and the control according to the same timetable. The tests were conducted as a blind test so that the order of doses would not affect the test results. In order to adapt the panels to the testing environment, the panels entered the testing room ten minutes before the commencement of the test, and calmed down to resting conditions before the test was started. When the test was started, the panels were kept under the resting conditions for fifteen (15) minutes, and then placed under the calculation work for thirty (30) minutes from the fifteenth (15th) minute to the forty-fifth (45th) minute from the commencement of the test. During the testing time (from 0 minute to the 45th minute), the blood pressure of the panels was measured continuously. Further, before the commencement of the test and after the termination of the calculation work, the panels were evaluated according to Profile of Mood State (POMS) method, which can evaluate the psychological conditions with the passage of time, in order to know their psychological conditions. The results of the tests were shown as follows: as to the blood pressure, by the change from the blood pressure in the resting condition; and as to the POMS, by the change from the points before the commencement of the test. The statistical differences were determined by paired t-test.

The fluctuation in the diastolic blood pressure during the testing period (from 0 minute to the 45th minute) is shown in FIG. 1. The diastolic blood pressure was elevated with the load of calculation work. In the case wherein the panels were given the anti-stress agent of the present invention, the rise in the diastolic blood pressure during loading of the calculation work stress was suppressed. Particularly, at the twentieth (20th) minute after the commencement of the test, the rise in the diastolic blood pressure was significantly suppressed as compared to that in the case of the controls with the significance level of 5% (*).

Figure 2:
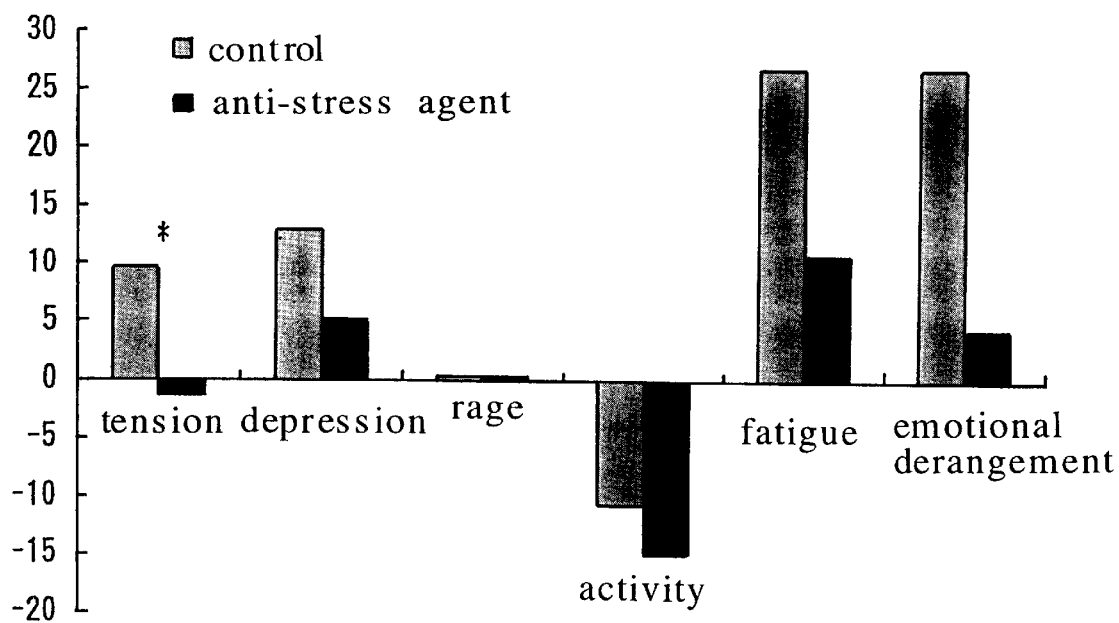
FIG. 2 is a graph showing the change in Profile of Mood State (POMS) after the termination of the mental arithmetic test in Experiment 1 in Example 1. The ordinate of the graph expresses the change in POMS score in percent (%)

The results of POMS test are shown in FIG. 2. It was recognized that, by comparing the results of the POMS test before the commencement of the test and after the calculation work, tension and depression tended to be relaxed, fatigue tended to be mitigated, and emotional derangement tended to be stabilized, in the case wherein the panels were given the anti-stress agent of the present invention. In particular, tension was significantly relaxed as compared to the controls with the significance level of 5% (*)

Experiment 2

Four (4) panels of healthy individuals (3 males, 1 female, age of 25 to 35) were given the anti-stress agent as a drink as mentioned above for seven (7) days in a row, and the mental arithmetic test was conducted before and after the uptake of the anti-stress agent.

On the first (1st) day, the mental arithmetic test was conducted on the panels from 10:30 a.m. in the same way as in Experiment 1. Subsequently, the panels were given 100 g of the anti-stress agent in the afternoon of the same day. From the second (2nd) day through the sixth (6th) day in a row, they were given 100 g of the anti-stress agent in the morning and in the afternoon. On the seventh (7th) day, the panels were given 100 g of the anti-stress agent at 7:00 a.m., and the same mental arithmetic test as in Experiment 1 was conducted on the panels from 10:30 a.m. The results of the test were shown by the change in the blood pressure and the heart rate from their resting conditions. The statistical differences were determined by paired t-test.

Figure 3:
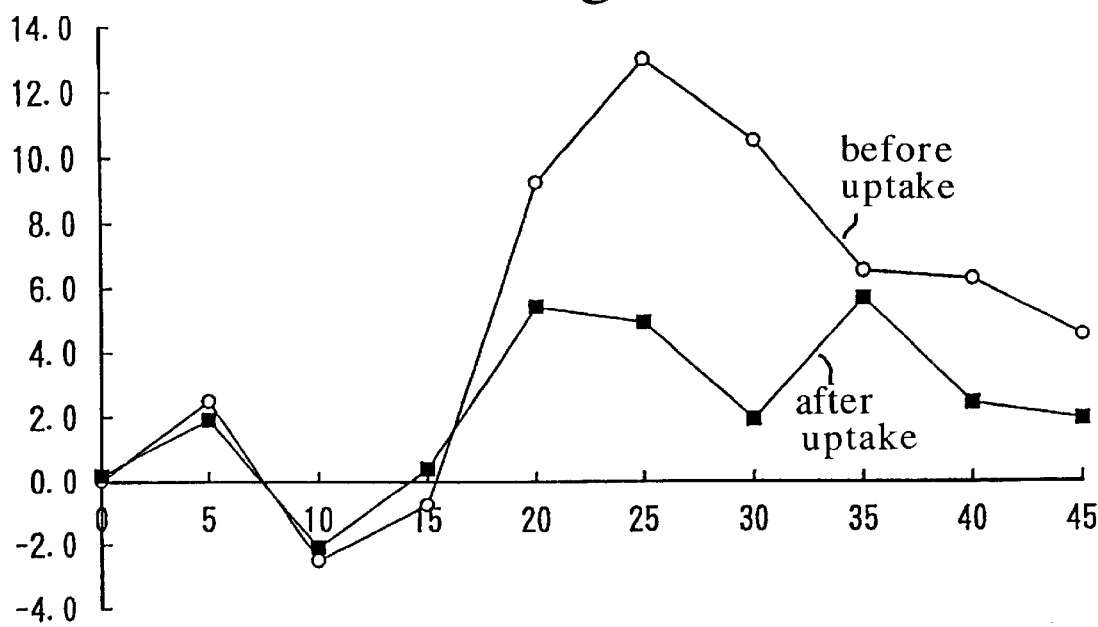
FIG. 3 is a graph showing the fluctuation in the diastolic blood pressure during the testing period of the mental arithmetic test when the panels were given fermented sour milk beverage for one week in Example 1. The ordinate of the graph expresses the diastolic blood pressure in mmHg, while the abscissa expresses the time in minute.
Figure 4:
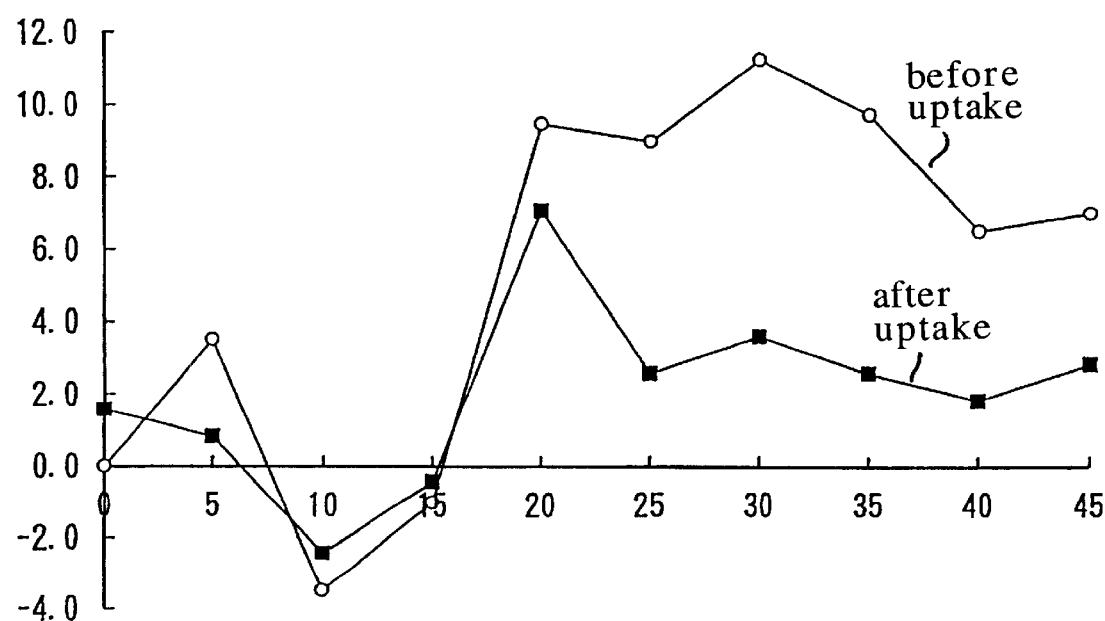
FIG. 4 is a graph showing the fluctuation in the heart rate during the testing period of the mental arithmetic test when the panels were give fermented sour milk beverage for one week in Example 1. The ordinate of the graph expresses the heart rate per minute in beat/min., while the abscissa expresses the time in minute.

The fluctuation in the diastolic blood pressure during the testing period (from 0 minutes to the 45th minutes) is shown in FIG. 3. The diastolic blood pressure was elevated with the load of calculation work. In the test after the panels were given the anti-stress agent of the present invention for one week in a row, the rise in the diastolic blood pressure during loading of the calculation work was suppressed as compared to that in the test conducted before the panels were given the anti-stress agent. Further, the fluctuation of the heart rate during the testing period (from 0 minute to the 45th minute) is shown in FIG. 4. The heart rate was elevated with the load of the calculation work. In the test after the panels were given the anti-stress agent of the present invention for one week in a row, the rise in the heart rate during loading of the calculation work was suppressed, as compared to that in the test conducted before the panels were given the anti-stress agent.

Example 2

The fermented sour milk prepared in Example 1 was sterilized under heating at 80° C. for 10 minutes. After that, starting materials were mixed to obtain a mixture having the composition of 75 weight % of the sterilized fermented sour milk, 13.3 weight % of 3 wt % HM pectin solution, 3.03 weight % of 30 wt % sodium citrate solution, 4.5 weight % of 1 wt % Aspartame solution, 0.25 weight % of blended flavor, and 3.92 weight % of water. The mixture was sterilized by heating up to 85° C., and then charged in brown bottles by 100 g each while hot, thereby producing fermented sour milk beverage. The obtained fermented sour milk beverage was subjected to the tests as in Example 1 to reveal that it has similar effects on blood pressure, heart rate, and POMS.

What is claimed is:

1. A method of ameliorating symptoms of tension, depression, fatigue and emotional derangement caused by stress which comprises administering to an animal in need of such treatment an anti-stress agent comprising microorganism-fermented sour milk to ameliorate tension, depression fatigue and emotional derangement, said microorganism comprising *Lactobacillus helveticus*.

2. The method of claim 1 wherein the anti-stress agent is administered at a dosage of at least 0.1 g dried product of the fermented sour milk per kilogram of body weight per day.

3. The method of claim 1 wherein the animal is a human.

* * * * *

UNITED STATES PATENT AND TRADEMARK OFFICE
CERTIFICATE OF CORRECTION

PATENT NO.    : 6,596,301 B1
DATED         : July 22, 2003
INVENTOR(S)   : Akihiro Masuyama et al.

It is certified that error appears in the above-identified patent and that said Letters Patent is hereby corrected as shown below:

<u>Title page,</u>
Item [73], Assignee, delete "Danone, Groupe" and substitute -- Groupe Danone --.

Signed and Sealed this

Twenty-third Day of December, 2003

JAMES E. ROGAN
*Director of the United States Patent and Trademark Office*